US008206992B2

(12) United States Patent
Reches et al.

(10) Patent No.: US 8,206,992 B2
(45) Date of Patent: Jun. 26, 2012

(54) COTTON THREAD AS A LOW-COST MULTI-ASSAY DIAGNOSTIC PLATFORM

(75) Inventors: Meital Reches, Somerville, MA (US); Michael D. Dickey, Cambridge, MA (US); Manish J. Butte, Boston, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/934,702

(22) PCT Filed: Mar. 27, 2009

(86) PCT No.: PCT/US2009/038702
§ 371 (c)(1),
(2), (4) Date: Jan. 26, 2011

(87) PCT Pub. No.: WO2009/121043
PCT Pub. Date: Oct. 1, 2009

(65) Prior Publication Data
US 2011/0189786 A1 Aug. 4, 2011

Related U.S. Application Data

(60) Provisional application No. 61/039,862, filed on Mar. 27, 2008.

(51) Int. Cl.
*G01N 21/77* (2006.01)
(52) U.S. Cl. ........ 436/169; 436/164; 436/514; 436/518; 436/530; 422/400; 422/401; 422/402; 422/405
(58) Field of Classification Search .................. None
See application file for complete search history.

(56) References Cited

U.S. PATENT DOCUMENTS
4,618,475 A 10/1986 Wang
(Continued)

FOREIGN PATENT DOCUMENTS
JP 08233799 A 9/1996
(Continued)

OTHER PUBLICATIONS

Aikio, et al., "Bioactive Paper and Fibre Products: Patent and Literary Survey," VTT Working Papers 51, VTT-Work-51, 2006, 84 pages.
(Continued)

*Primary Examiner* — Yelena G Gakh
*Assistant Examiner* — Robert Xu
(74) *Attorney, Agent, or Firm* — Wilmer Cutler Pickering Hale and Dorr LLP

(57) ABSTRACT

Hydrophilic threads as platforms for inexpensive, low volume, portable diagnostic systems, and methods of making the same are described. A diagnostic system includes a hydrophilic loading thread having an inlet zone at a proximal end; a testing zone at a distal end; and an intermediate zone located between the inlet zone and the testing zone, wherein the testing zone does not directly contact the inlet zone. In another aspect, a diagnostic system includes (i) a hydrophilic loading thread that includes an inlet zone at a proximal end and an intermediate zone at a distal end; and (ii) one or more additional hydrophilic threads that contact the intermediate zone of the loading thread. A method of detecting the presence or absence of an analyte in a fluid sample includes applying the sample to an inlet zone of a diagnostic system that includes a hydrophilic loading thread with an inlet zone at a proximal end; an intermediate zone; and a testing zone at a distal end; wherein the testing zone does not directly contact the inlet zone.

18 Claims, 12 Drawing Sheets

U.S. PATENT DOCUMENTS

| | | | |
|---|---|---|---|
| 4,668,564 A | 5/1987 | Orchard | |
| 4,668,619 A | 5/1987 | Greenquist et al. | |
| 4,743,530 A | 5/1988 | Farid et al. | |
| 4,757,004 A | 7/1988 | Houts et al. | |
| 4,861,711 A | 8/1989 | Friesen et al. | |
| 5,120,544 A | 6/1992 | Henley | |
| 5,209,904 A | 5/1993 | Forney et al. | |
| 5,266,179 A | 11/1993 | Nankai et al. | |
| 5,279,944 A | 1/1994 | Fabrizi et al. | |
| 5,409,664 A | 4/1995 | Allen | |
| 5,648,252 A | 7/1997 | Dumitriu et al. | |
| 5,707,818 A | 1/1998 | Chudzik et al. | |
| 5,834,226 A | 11/1998 | Maupin | |
| 5,858,392 A | 1/1999 | Dumitriu et al. | |
| 5,869,172 A | 2/1999 | Caldwell | |
| 5,897,522 A | 4/1999 | Nitzan | |
| 5,906,934 A | 5/1999 | Grande et al. | |
| 5,925,259 A | 7/1999 | Biebuyck et al. | |
| 5,941,862 A | 8/1999 | Haynes et al. | |
| 6,004,442 A | 12/1999 | Choulga et al. | |
| 6,025,203 A | 2/2000 | Vetter et al. | |
| 6,060,534 A | 5/2000 | Ronan et al. | |
| 6,180,239 B1 | 1/2001 | Whitesides et al. | |
| 6,202,471 B1 | 3/2001 | Yadav et al. | |
| 6,210,907 B1 | 4/2001 | Cha | |
| 6,284,072 B1 | 9/2001 | Ryan et al. | |
| 6,319,310 B1 | 11/2001 | Wong et al. | |
| 6,391,523 B1 | 5/2002 | Hurditch et al. | |
| 6,416,642 B1 | 7/2002 | Alajoki et al. | |
| 6,440,645 B1 | 8/2002 | Yon-Hin et al. | |
| 6,440,725 B1 | 8/2002 | Pourahmadi et al. | |
| 6,478,938 B1 | 11/2002 | Paek et al. | |
| 6,566,575 B1 | 5/2003 | Stickels et al. | |
| 6,642,408 B2 | 11/2003 | Batlaw et al. | |
| 6,761,962 B2 | 7/2004 | Bentsen et al. | |
| 6,816,125 B2 | 11/2004 | Kuhns et al. | |
| 6,844,200 B2 | 1/2005 | Brock | |
| 6,877,892 B2 | 4/2005 | Karp | |
| 6,880,576 B2 | 4/2005 | Karp et al. | |
| 6,887,701 B2 | 5/2005 | Anderson et al. | |
| 6,919,046 B2 | 7/2005 | O'Connor et al. | |
| 6,931,523 B1 | 8/2005 | Tomoson et al. | |
| 6,935,772 B2 | 8/2005 | Karp et al. | |
| 6,951,682 B1 | 10/2005 | Zebala | |
| 6,951,757 B2 | 10/2005 | Sabatini | |
| 6,989,128 B2 | 1/2006 | Alajoki et al. | |
| 7,008,799 B1 | 3/2006 | Zimmer et al. | |
| 7,186,352 B2 | 3/2007 | Morse et al. | |
| 7,291,857 B2 | 11/2007 | Tanaka et al. | |
| 7,303,923 B2 | 12/2007 | Hardman et al. | |
| 2002/0187560 A1 | 12/2002 | Pezzuto et al. | |
| 2003/0032203 A1 | 2/2003 | Sabatini et al. | |
| 2003/0148401 A1 | 8/2003 | Agrawal et al. | |
| 2004/0067166 A1 | 4/2004 | Karinka et al. | |
| 2004/0103808 A1 | 6/2004 | Lochun et al. | |
| 2005/0145496 A1 | 7/2005 | Goodsaid et al. | |
| 2005/0169962 A1 | 8/2005 | Bhatia et al. | |
| 2005/0196702 A1 | 9/2005 | Bryant et al. | |
| 2005/0266582 A1 | 12/2005 | Modlin et al. | |
| 2006/0014003 A1 | 1/2006 | Libera et al. | |
| 2006/0038182 A1 | 2/2006 | Rogers et al. | |
| 2006/0088857 A1 | 4/2006 | Attiya et al. | |
| 2006/0130054 A1 | 6/2006 | Bocking et al. | |
| 2006/0226575 A1 | 10/2006 | Maghribi et al. | |
| 2007/0179117 A1 | 8/2007 | Reiner et al. | |
| 2007/0196819 A1 | 8/2007 | Asberg et al. | |
| 2007/0224701 A1 | 9/2007 | Rosenstein | |
| 2007/0278097 A1 | 12/2007 | Bhullar et al. | |
| 2007/0298433 A1 | 12/2007 | Sia et al. | |
| 2009/0298191 A1 | 12/2009 | Whitesides et al. | |
| 2011/0111517 A1 | 5/2011 | Siegel et al. | |
| 2011/0123398 A1 | 5/2011 | Carrilho et al. | |

FOREIGN PATENT DOCUMENTS

| | | |
|---|---|---|
| WO | WO-97/48257 | 12/1997 |
| WO | WO-99/46644 | 9/1999 |
| WO | WO-00/33078 | 6/2000 |
| WO | WO-01/02093 A2 | 1/2001 |
| WO | WO-01/25138 | 4/2001 |
| WO | WO-03/015890 A1 | 2/2003 |
| WO | WO-2004/006291 A2 | 1/2004 |
| WO | WO-2004/080138 | 9/2004 |
| WO | WO-2005/090975 A1 | 9/2005 |
| WO | WO-2005/090983 A2 | 9/2005 |
| WO | WO-2005/107938 | 11/2005 |
| WO | WO-2005/109005 A1 | 11/2005 |
| WO | WO-2006/076703 | 7/2006 |
| WO | WO-2007/029250 | 3/2007 |
| WO | WO-2007/081848 | 7/2007 |
| WO | WO-2007/116056 | 10/2007 |
| WO | WO-2008/049083 | 4/2008 |
| WO | WO-2009/121037 A2 | 10/2009 |
| WO | WO-2009/121038 | 10/2009 |
| WO | WO-2009/121041 A2 | 10/2009 |
| WO | WO-2009/121043 A2 | 10/2009 |
| WO | WO-2010/022324 | 2/2010 |
| WO | WO-2010/102279 A1 | 9/2010 |
| WO | WO-2010/102294 A1 | 9/2010 |

OTHER PUBLICATIONS

Author Unknown, "Focus: Lab on Paper, DOI: 10.1039/b814043j," Lab Chip, vol. 8, No. 12, Dec. 2008, pp. 1988-1991, XP002585318, The Royal Society of Chemistry.

Berggren, et al., "Paper Electronics and Electronic Paper," IEEE, Section 12: Flexible Systems, 2001, pp. 300-303.

Bracher, et al., "Heterogeneous Films of Ionotropic Hydrogels Fabricated from Delivery Templates of Patterned Paper," Adv. Mater., 2008, pp. 1807-1812.

Brooks, et al., "A Simple Artificial Urine for the Growth of Urinary Pathogens," Lett. Appl. Microbiol., 1997, 24, pp. 203-206.

Bruzewicz, et al., "Low-Cost Printing of Poly(dimethylsiloxane) Barriers to Define Microchannels in Paper," Anal. Chem., 2008, 80, pp. 3387-3392.

Bruzewicz, et al., "Paper: Fabrication of a Modular Tissue Construct in a Microfluidic Chip," Lab Chip, 2008, 8, pp. 663-671.

Campana, et al., "Double and Triple Staining Methods for Studying the Proliferative Activity of Human B and T Lymphoid Cells," Journal of Immunological Methods, 107, 1988, pp. 79-88.

Carrilho, et al., "Paper Microzone Plates," Analytical Chemistry, vol. 81, No. 15, Aug. 2009, pp. 5990-5998.

Carrilho, et al., "Understanding Wax Printing: A Simple Micropatterning Process for Paper-Based Microfluidics," Analytical Chemistry, vol. 81, No. 16, Aug. 2009, pp. 7091-7095.

Chadee, et al., "Increased Phosphorylation of Histone H1 in Mouse Fibroblasts Transformed with Oncogenes or Constitutively Active Mitogen-Activated Protein Kinase Kinase," The Journal of Biological Chemistry, vol. 270, No. 34, Aug. 1995, pp. 20098-20105.

Cheng, et al., "Clinical Analytics: Paper-Based ELISA**," Agnew. Chem., 2010, 122, pp. 1-5.

Chin, et al., "Lab-on-a-chip Devices for Global Health: Past Studies and Future Opportunities," Lab Chip, 2007, 7, pp. 41-57, A Journal of the Royal Society of Chemistry.

Costerton, et al., "Bacterial Biofilms: a Common Cause of Persistent Infections," Science Mag., 1999, pp. 1318-1322.

Daar, et al., "Top Ten Biotechnologies for Improving Health in Developing Countries," Nature Genetics, vol. 32, Oct. 2002, pp. 229-232.

Donlan, "Biofilm Formation: A Clinically Relevant Microbiological Process," Healthcare Epidemiology, CID 2001:33, Oct. 2001, pp. 1387-1392.

Donlan, et al., "Biofilm Formation on Cast Iron Substrata in Water Distribution Systems," Wat. Res. vol. 28, No. 6, pp. 1497-1503, 1994.

Donlan, et al., "Reviews: Biofilms: Survival Mechanisms of Clinically Relevant Microorganisms," Clinical Microbiology Reviews, vol. 15, No. 2, Apr. 2002, pp. 167-193.

Dungchai, et al., "Electrochemical Detection for Paper-Based Microfluidics," Anal. Chem., 2009, 81, pp. 5821-5826.

Ebeling, "The Permanent Life of Connective Tissue Outside of the Organism," J. Exp. Med., 17, 1913, 15 pages.

Harrison, et al., "Methodology Article: High-Throughput Metal Susceptibility Testing of Microbial Biofilms," BMC Microbiology, 2005, 5:53, 11 pages.

International Search Report and Written Opinion of the International Searching Authority, the European Patent Office, for International Application No. PCT/US2007/081848, dated Jan. 28, 2009, 12 pages.

International Search Report and Written Opinion of the International Searching Authority, the European Patent Office, for PCT/US2010/026499, dated Jun. 16, 2010, 2 pages.

International Search Report and Written Opinion of the International Searching Authority, the Korean Intellectual Property Office, for International Application No. PCT/US2009/038566, dated Dec. 16, 2009, 10 pages.

International Search Report and Written Opinion of the International Searching Authority, the Korean Intellectual Property Office, for International Application No. PCT/US2009/038694 dated Nov. 12, 2009, 10 pages.

International Search Report and Written Opinion of the International Searching Authority, the Korean Intellectual Property Office, for PCT/US2009/038693, dated Oct. 28, 2009, 8 pages.

International Search Report and Written Opinion of the International Searching Authority, the Korean Intellectual Property Office, for PCT/US2009/038699, dated Oct. 28, 2009, 9 pages.

International Search Report and Written Opinion of the International Searching Authority, the Korean Intellectual Property Office, for PCT/US2009/038702, dated Nov. 11, 2009, 7 pages.

International Search Report of the International Searching Authority, the European Patent Office, for PCT/US2010/026547, dated Jul. 19, 2010, 3 pages.

International Search Report of the International Searching Authority, the Korean Intellectual Property Office, for PCT/US2009/054601, dated Mar. 22, 2010, 2 pages.

Klajn, et al., "Multicolour Micropatterning of Thin Films and Dry Gels," Nature Materials, vol. 3, Oct. 2004, pp. 729-735.

Lahav, et al., "DOI: 10.1002/adma.200601843—Patterning of Poly(acrylic acid) by Ionic Exchange Reactions in Microfluidic Channels**," Advanced Materials, 2006, 18, pp. 3174-3178.

Leary, et al., "Rapid and Sensitive Colorimetric Method for Visualizing Biotin-Labeled DNA Probes Hybridized to DNA or RNA Immobilized on Nitrocellulose: Bio-Blots," PNAS, vol. 80, No. 13, 1983, pp. 4045-4049.

Li, et al., "Thread as a Versatile Material for Low-Cost Microfluidic Diagnostics," Applied Materials & Interfaces, vol. 2, No. 1, Jan. 2010, 6 pages.

Liu, et al., "Three-Dimensional Photopatterning of Hydrogels Containing Living Cells," Biomed. Microdevices, 2002, 4, pp. 257-266.

Lu, et al., "Short Communication: Rapid Prototyping of Paper-Based Microfluidics with Wax for Low-Cost, Portable Bioassay," Electrophoresis, 2009, 30, pp. 1497-1500.

Mabey, et al., "Diagnostics for the Developing World," Nature Reviews / Microbiology, vol. 2, Mar. 2004, pp. 231-240.

Martinez, et al., "Diagnostics for the Developing World: Microfluidic Paper-Based Analytical Devices," Analytical Chemistry, vol. 82, No. 1, Jan. 2010, pp. 3-10.

Martinez, et al., "FLASH: A Rapid Method for Prototyping Paper-Based Microfluidic Devices," Lab Chip, 2008, 8, pp. 2146-2150, A Journal of The Royal Society of Chemistry.

Martinez, et al., "Paper: Programmable Diagnostic Devices Made from Paper and Tape," Lab Chip, Jul. 2010, 6 pages.

Martinez, et al., "Patterned Paper as a Platform for Inexpensive, Low-Volume, Portable Bioassays**," Agnew. Chem. Int. Ed., 2007, 46, pp. 1318-1320.

Martinez, et al., "Simple Telemedicine for Developing Regions: Camera Phones and Paper-Based Microfluidic Devices for Real-Time, Off-Site Diagnosis," Analytical Chemistry, vol. 80, No. 10, May 2008, pp. 3699-3707.

Martinez, et al., "Three-Dimensional Microfluidic Devices Fabricated in Layered Paper and Tape," PNAS, vol. 105, No. 50, Dec. 2008, pp. 19606-19611.

Matsumoto, et al., "Three-Dimensional Cell and Tissue Patterning in a Strained Fibrin Gel System," PLoS One, Nov. 2007, Issue No. 11, 6 pages.

Nelson, et al., "Three-Dimensional Lithographically Defined Organotypic Tissue Arrays for Quantitative Analysis of Morphogenesis and Neoplastic Progression," Nature Protocols, vol. 3, No. 4, 2008, pp. 674-678.

Nie et al., "Paper: Integration of Paper-based Microfluidic Devices with Commercial Electrochemical Readers," Lab Chip, Oct. 2010, 7 pages.

Peele, et al., "Semi-Automated vs. Visual Reading of Urinalysis Dipsticks," Clin. Chem, 1977, 23, pp. 2242-2246.

Pugia, et al., "High-Sensitivity Dye Binding Assay for Albumin in Urine," J. Clin. Lab. Anal. 1999, 13, pp. 180-187.

Reches, et al., "Thread as a Matrix for Biomedical Assays," Applied Materials & Interfaces, vol. xxx, No. xx, 000, xxxx, pp. A-G, 2010.

Shaw, et al., "Negative Photoresists for Optical Lithography," IBM Journal of Research and Development, vol. 41, No. 1/2, Jan./Mar. 1997, pp. 81-94, 15 pages.

Shimizu, et al., "Biofilm Formation on Hydrophilic Intraocular Lens Material," Current Eye Research, 31, 2006, pp. 989-997.

Sia, et al., "Microfluidic Devices Fabricated in Poly(dimethylsiloxane) for Biological Studies," Electrophoresis, 2003, 24, pp. 3563-3576.

Siegel, et al., "Foldable Printed Circuit Boards on Paper Substrates," Advanced Functional Materials, 2010, 20, pp. 28-35.

Smith, S.K., "Angiogenesis, Vascular Endothelial Growth Factor and the Endometrium," Hum. Reprod. Update 1998, 4, pp. 509-519.

Tang, et al., "Molding of Three-Dimensional Microstructures of Geis," J. Am. Chem. Soc., 2003, 125, pp. 12988-12989.

Urbich, et al., "Endothelial Progenitor Cells: Characterization and Role in Vascular Biology," Circulation Research, DOI: 10.1161/01.RES.0000137877.89448.78, Aug. 2004, pp. 343-353.

von Lode, P., "Point-of-care Immunotesting: Approaching the Analytical Performance of Central Laboratory Methods," Clinical Biochemistry, 38, 2005, pp. 591-606.

Washburn, E. W., "The Dynamics of Capillary Flow," The Physical Review, vol. XVII, No. 3, Second Series, Mar. 1921, pp. 273-283.

Winkleman, et al., "Patterning micron-sized features in a cross-linked poly (acrylic acid) film by a wet etching process," The Royal Society of Chemistry, 2007, pp. 108-116.

Xerox Corporation, "Material Safety Data Sheet for Xerox Phaser 6250 Color Laser Toner," 2003, pp. E-1-E-5, retrieved from http://www.office.xerox.com/userdoc/P6250/6250_Web/pdfs/msds.pdf.

Zhi, et al., "Multianalyte Immunoassay with Self-Assembled Addressable Microparticle Array on a Chip," Analytical Biochemistry, vol. 318, No. 2, Jul. 2003, pp. 236-243.

Zhu, et al., "Research Article: Proposal to Create Subspecies of *Rickettsia conorii* Based on Multi-Locus Sequence Typing and an Emended Description of *Rickettsia conorii*," BMC Microbiology, 2005, 5:11, 11 pages.

Translation of First Office Action dated Jan. 11, 2012 as received from associate, Seiwa Patent & Law on Feb. 21, 2012 for Japanese Patent Application No. 2009/533543, 11 pages.

a)

b)

US 8,206,992 B2

COTTON THREAD AS A LOW-COST MULTI-ASSAY DIAGNOSTIC PLATFORM

CROSS-REFERENCE TO RELATED APPLICATIONS

This application claims the benefit of U.S. Provisional Application No. 61/039,862, filed Mar. 27, 2008, the contents of which are hereby incorporated in their entirety herein.

STATEMENT AS TO FEDERALLY SPONSORED RESEARCH

This invention was made with the support under GM065364 awarded by the National Institute of Health. The government has certain rights in the invention.

BACKGROUND

Most current bioanalytical assays are inaccessible to developing economies. Current diagnostic assays typically require large and expensive laboratory instruments that are operated by trained personnel. Although "dipstick" technologies have increased the accessibility of many assays, many of the assays are too expensive for low-cost settings and often require relatively large sample volumes. Thus, there remains a need for low-cost diagnostic assays that are not cumbersome and that can be performed on small sample volumes.

SUMMARY

Hydrophilic threads as platforms for inexpensive, low volume, portable diagnostic systems, and methods of making the same are described. Under certain aspects, the diagnostic systems are constructed by positioning hydrophilic threads within a laminated structure. This type of thread diagnostic is convenient for running low-cost, portable, and technically simple multiplexed bioassays. An illustrative embodiment is described in which the thread diagnostic is used for the simultaneous detection of glucose and protein in 20 µL of artificial urine. Under many aspects, the diagnostic system is small, disposable, easy to use (and carry), and requires no external equipment, reagents, or power sources. This kind of diagnostic system is attractive for uses in developing countries, in the field, and/or as an inexpensive alternative to more advanced technologies already used in clinical settings.

Accordingly, in one aspect, a diagnostic system includes a hydrophilic loading thread having an inlet zone at a proximal end; a testing zone at a distal end; and an intermediate zone located between the inlet zone and the testing zone, wherein the testing zone does not directly contact the inlet zone. In some embodiments, the system includes one or more additional hydrophilic threads that contact the intermediate zone of the loading thread, where the additional threads include testing zones. In one or more embodiments, the testing zone is treated with a detection reagent to provide a visible indication of an analyte present in a fluid sample.

In another aspect, a diagnostic system includes (i) a hydrophilic loading thread that includes an inlet zone at a proximal end and an intermediate zone at a distal end; and (ii) one or more additional hydrophilic threads that contact the intermediate zone of the loading thread. In some embodiments, one or more of the additional hydrophilic threads include a testing zone.

In another aspect, a method of detecting the presence or absence of an analyte in a fluid sample includes applying the sample to an inlet zone of a diagnostic system that includes a hydrophilic loading thread with an inlet zone at a proximal end; an intermediate zone; and a testing zone at a distal end; wherein the testing zone does not directly contact the inlet zone.

As used herein, an "inlet zone" is an area of a hydrophilic thread where a biological sample is applied or loaded onto a diagnostic system.

As used herein, a "loading thread" is a hydrophilic thread that includes at least an inlet zone and an intermediate zone. After the sample is applied to the inlet zone, the sample is carried through the loading thread from the inlet zone through the intermediate zone by capillary action. In some embodiments, the loading thread further includes a testing zone, which is physically separated from the inlet zone by the intermediate zone.

As used herein, an "intermediate zone" is an area of a hydrophilic thread distal to an inlet zone. In some embodiments, an intermediate zone is oriented between an inlet zone and a testing zone on a hydrophilic thread. In other embodiments, a hydrophilic thread includes an inlet zone at a proximal end and terminates in an intermediate zone at a distal end.

As used herein, a "testing zone" or "detection zone" is an area of a hydrophilic thread that is treated with a detection reagent.

BRIEF DESCRIPTION OF THE DRAWINGS

The foregoing and other objects of the present invention, the various features thereof, as well as the invention itself, may be more fully understood from the following description, when read together with the accompanying drawings, in which.

DETAILED DESCRIPTION

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

I. Diagnostic Systems

The methods and compositions described herein relate to diagnostic systems that utilize hydrophilic threads to assay fluid samples. No external power source is necessary to perform the assays, as capillary action rapidly draws the sample along the thread and into testing zones used in the assays. Further, the assays can be conducted rapidly, on the order of minutes.

Figure 1:
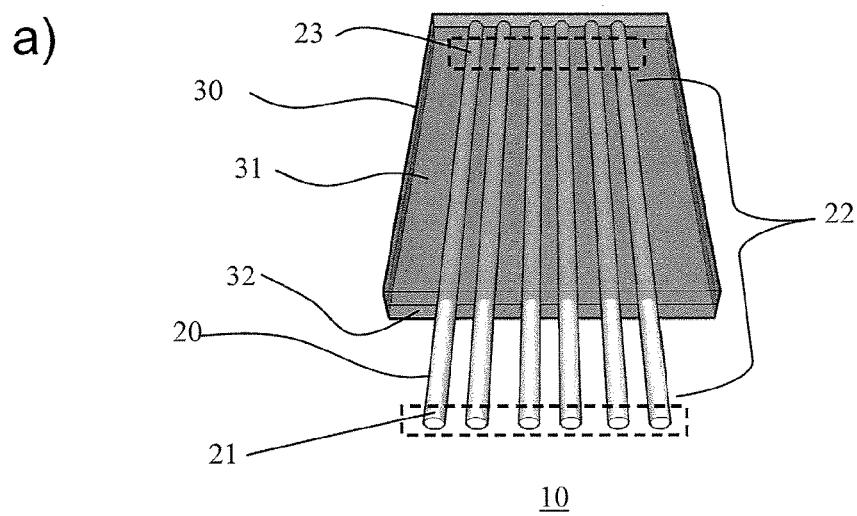
FIG. 1A is a schematic illustration of a "woven array" diagnostic system.
FIG. 1B is a schematic illustration of a "branching array" diagnostic system.
FIG. 1C is a schematic illustration of a "sewn array" diagnostic system.
Figure 1:
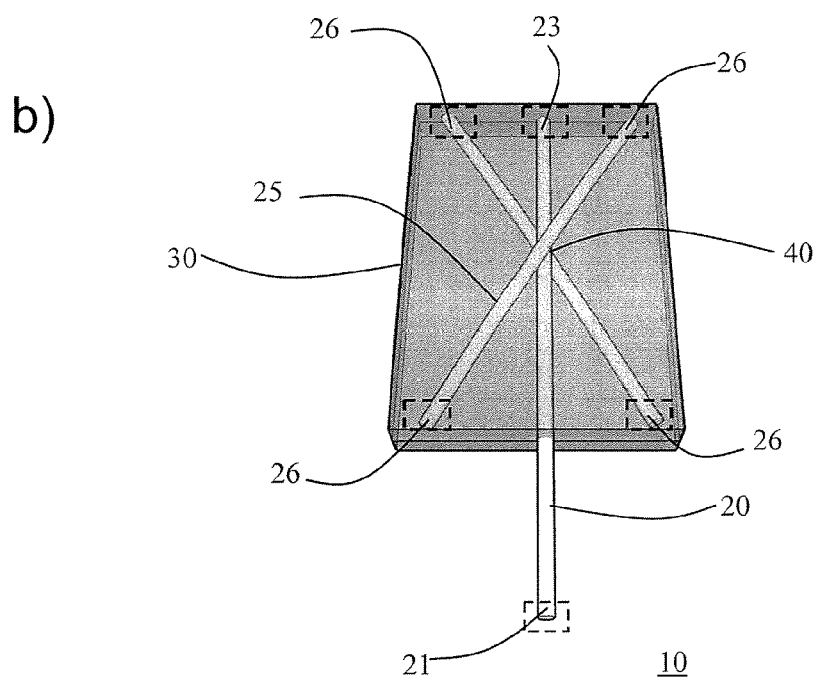
Figure 1:
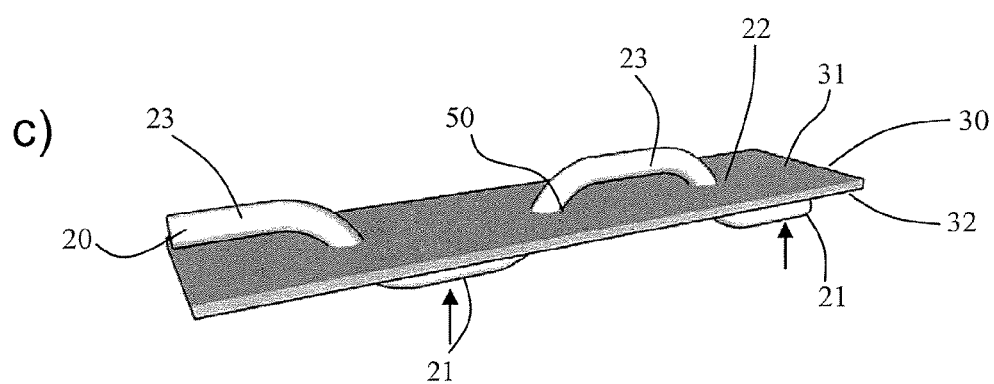

With reference to FIGS. 1A, 1B, and 1C, a few nonlimiting configurations of a diagnostic system 10 are illustrated therein. In the illustrated configurations, the system 10 generally includes loading threads 20 and a housing 30.

FIG. 1A illustrates a "woven array" configuration. With reference to FIG. 1A, a diagnostic system 10 includes loading threads 20 and a housing 30. The loading threads 20 and housing 30 are configured such that a proximal end of each loading thread 20 is exposed and a distal end of each loading thread 20 is enclosed within housing 30.

Loading thread 20 comprises an inlet zone 21, intermediate zone 22, and testing zone 23. Inlet zone 21 is at the proximal end of loading thread 20 and is not disposed within housing 30. Intermediate zone 22 encompasses the entire region of loading thread 20 between inlet zone 21 and testing zone 23. In FIG. 1A, a proximal end of intermediate zone 22 is not disposed within housing 30, and a distal end of intermediate zone 22 is disposed within housing 30. Testing zones 23 include one or more detection reagents described herein.

FIG. 1B illustrates a "branching array" configuration. With reference to FIG. 1B, a diagnostic system 10 includes loading thread 20, testing threads 25, and a housing 30. Loading thread 20 and housing 30 are configured such that a proximal end of loading thread 20 is exposed and a distal end of loading thread 20 is disposed within housing 30. Testing threads 25 are disposed within housing 30 and intersect loading thread 20 at branching point 40.

Loading thread 20 comprises an inlet zone 21, intermediate zone 22, and testing zone 23. Inlet zone 21 is at the proximal end of loading thread 20 and is not disposed within housing 30. Intermediate zone 22 encompasses the entire region of loading thread 20 between inlet zone 21 and testing zone 23. In FIG. 1B, a proximal end of intermediate zone 22 is not disposed within housing 30, and a distal end of intermediate zone 22 is disposed within housing 30. Intermediate zone 22 intersects testing threads 25 at branching point 40. Testing threads 25 comprise intermediate zones that intersect with intermediate zone 22 at branching point 40, and the ends of testing threads 25 comprise testing zones 26. Testing zones 23 and 26 include one or more detection reagents described herein.

FIG. 1C illustrates a "sewn array" configuration. With reference to FIG. 1C, a diagnostic system 10 includes loading thread 20 and a housing 30. Housing 30 comprises a top face 31 and a bottom face 32. Loading thread 20 is disposed onto housing 30 such that testing zones 23 of loading thread 20 are disposed on and exposed at the top face 31 of housing 30 and inlet zones 21 of loading thread 20 are disposed on and exposed at the bottom face 32 of housing 30. Loading thread 20 includes intermediate zones 22 located between inlet zones 21 and testing zones 23. A proximal end of intermediate zone 22 is exposed on the bottom face 32 of housing 30 and a distal end of intermediate zone 22 is exposed on the top face 31 of housing 30. The distal end of testing zone 23 contacts linker region 50 of thread 20. Linker region 50 contacts the top face 31 of housing 30, passes through housing 30, and contacts the bottom face 32 of housing 30. The distal end of linker region 50 contacts the next inlet zone 21 of thread 20. Testing zones 23 include one or more detection reagents described herein.

The diagnostic systems described herein include a housing 30. The housing can be made of plastic or any other inert material that does not interfere with the assay procedure. For example, the housing can be any known flexible sheet or molded plastic. Preferably, the housing is made of tape. The housing can be used as a support to maintain the hydrophilic threads in the appropriate configurations. The housing can also protect the hydrophilic threads from contamination and mechanical damage during handling and storage. Further, as described herein, the housing can be used to seal and separate one or more hydrophilic threads from each other to prevent cross-contamination.

In some embodiments, e.g., "woven array" or "branching array" configurations, at least one face of the housing is made of a transparent material. In some embodiments, e.g., "sewn array" configurations, the housing can be a substrate, such as an adhesive bandage, paper, cloth, or clothing.

Figure 2:
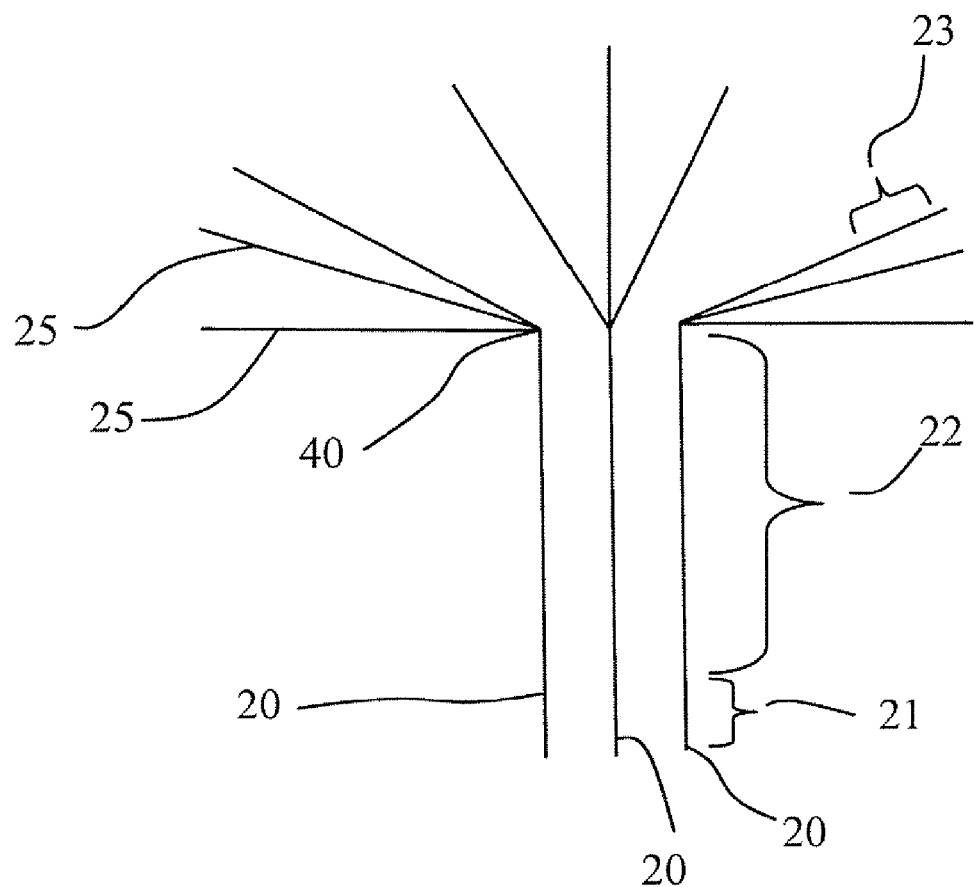
FIG. 2 is a schematic illustration of an additional embodiment of a thread-based diagnostic system.

The diagnostic systems described herein can include various additional configurations. For example, the proximal ends of hydrophilic threads can be braided to perform multiple assays on a fluid sample. As depicted in FIG. 2, diagnostic system 10 can include three hydrophilic loading threads 20, each of which contacts testing threads 25 at branching points 40. Loading threads 20 and testing threads 25 include testing zones 23, resulting in 9 separate testing zones. Although FIG. 2 depicts the loading threads 20 in a linear orientation, in other embodiments, the inlet zones of loading threads 20 or the inlet zones and at least a portion of intermediate zones of loading threads 20 can be braided or can be brought together to facilitate simultaneous loading of a sample.

Figure 3:
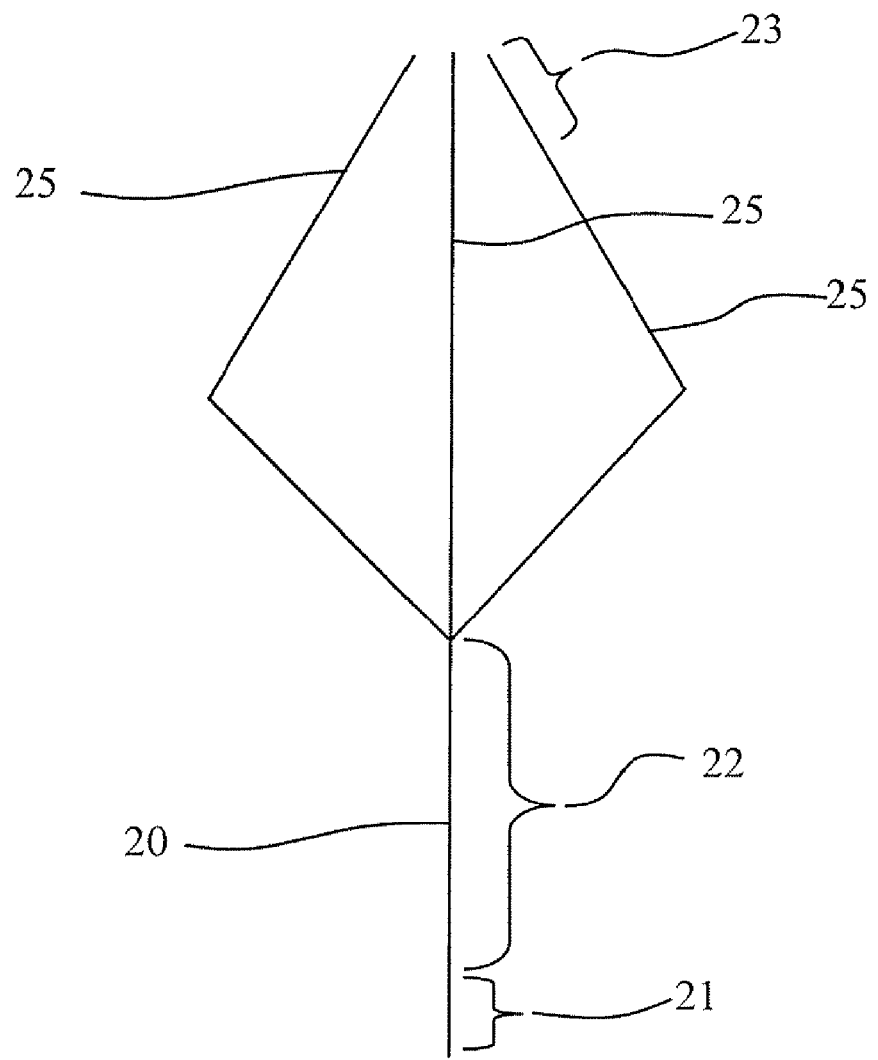
FIG. 3 is a schematic illustration of an additional embodiment of a thread-based diagnostic system.

In other embodiments, the diagnostic system has a configuration depicted in FIG. 3. In this configuration, the diagnostic system includes loading thread 20 with inlet zone 21 and intermediate zone 22 that contacts testing threads 25, each of which includes a testing zone 23 having the same detection reagent. The distal ends of testing threads 25 combined. In some embodiments, the distal ends of testing threads 25 are braided. Such a configuration can be used, e.g., to provide a combined detectable signal can be used to assay fluid samples containing small concentrations of analytes.

Hydrophilic Threads

Threads 20 and 25 described herein can be of any hydrophilic material that wicks fluid by capillary action. For example, cotton, nylon, polyester, polyolefins (such as polypropylene), fluoropolymers (such as polyvinylidene fluoride), nitrocellulose, cellulose, cellulose acetate, and glass microfiber structures can be used in the diagnostic systems described herein.

Preferably, the threads are made of cotton, which is inexpensive, available worldwide, and is an established material (e.g., in the form of gauze) in hospitals because of its biocompatibility. Thread is durable under many environmental conditions, yet flexible and light weight; these properties correspond with the potential for ubiquitous use, as well as easy transport and storage (e.g., as light weight reels). Cotton thread wicks most non-viscous, water-based biological fluids while simultaneously filtering particulates.

The threads have dimensions that exhibit a high-aspect ratio (length:diameter). Such a high-aspect ratio reduces lateral flow within the thread. The lack of lateral transport reduces the required volume of sample (e.g., the volume of blood from a finger prick is likely to be sufficient) and focuses the assay signal (i.e., the analyte wicks to the end of the thread, increasing the local concentration and therefore the signal).

In some embodiments, the hydrophilic thread is functionalized to enhance the absorptive and/or wicking properties using any of a number of known substances and methods. For example, the hydrophilic threads can be exposed to oxygen plasma (SPI Plasma-Prep II, Structure Probe, Inc.) or to a mercerization process (exposure of the thread to NaOH while under tension).

Detection Reagents

The diagnostic systems described herein can contain hydrophilic threads that include diagnostic reagents capable of reacting with a predetermined analyte whose presence is suspected in a sample to be assayed. In some embodiments, the hydrophilic threads (e.g., testing zones) can be treated with one or more detection reagents before the diagnostic system is assembled. For example, a detection reagent can be spotted onto one end of a thread and allowed to be incorporated into the thread by capillary action. The thread can subsequently be dried, and the area of the thread contacted by the detection reagent results in a testing zone.

The interaction or complex of a detection reagent and a predetermined analyte within a fluid sample can generate a detectable effect, for example one that is apparent to the naked eye (e.g., detected as a color change). Alternatively, such an interaction can be detected using a spectrometer or other technical means (e.g., to detect a change in ultraviolet absorption).

Typically, the detection reagent has a greater affinity for the predetermined analyte than for other components of the fluid sample to be assayed. The detection reagent can be a chemical, which undergoes a color change when contacted with a particular analyte, or an enzyme that can convert an analyte into a detectable compound or can convert a second agent into a detectable compound in the presence of an analyte.

In some embodiments, the detection reagent is an immunoglobulin, e.g., an antibody, e.g., a primary antibody, that specifically binds to a particular analyte. In some embodiments, a detection antibody, e.g., a secondary antibody, can be loaded onto the diagnostic system after the fluid sample is loaded. When the detection reagent, e.g., primary antibody, specifically binds to an analyte in the fluid and a detection antibody is subsequently loaded onto the diagnostic system, the detection antibody can specifically bind to an analyte bound to the primary antibody and can provide a detectable signal.

In some embodiments, a diagnostic system includes many detection reagents, each of which can react with a different analyte to produce a detectable effect. Alternatively, each detection reagent can be sensitive only to a predetermined concentration of a single analyte.

In some embodiments, the detection reagent is disposed along the testing zone of a hydrophilic thread and is freely mobile when contacted by the fluid sample. In such embodiments, the detection reagent is carried through the hydrophilic thread to the end of the thread, e.g., by capillary action, allowing detection of an analyte to occur at the end of the thread (e.g., testing zone). In other embodiments, the detection reagent is disposed at the end of a thread and the fluid sample is carried through the hydrophilic thread to the detection reagent at the end of the thread. In certain embodiments, detection can occur as the concentration of analyte that reaches the end of the testing zone increases due to capillary action, resulting in an increase in detectable effect produced by the detection reagent. In some embodiments, the biological sample evaporates at the end of the testing zone, resulting in a continued amount of biological sample being wicked through the hydrophilic thread to the end of the testing zone. This can result in increasing amounts of analyte being carried to the detection reagent at the end of the testing zone and an increase in the detectable effect.

II. Methods of Using Diagnostic Systems

The diagnostic systems described herein can be used to test for the presence of analytes in fluid samples. With reference to FIG. 1A, the diagnostic system 10 can be loaded with a fluid sample by contacting the fluid sample with the inlet zone 21 on thread 20. The fluid sample is then transported through thread 20 by wicking action from the inlet zone 21 to intermediate zone 22. The fluid is transported through intermediate zone 22 to testing zone 23 by wicking action. Testing zone 23 includes a detection reagent described herein, e.g., a detection reagent for a specific analyte. The interaction of a predetermined analyte within the fluid sample with the detection reagent results in a detectable signal at testing zone 23.

In certain embodiments, testing zones 23 include the same detection reagent. In other embodiments, at least one testing zone 23 includes a detection reagent that is different from the detection reagent on a second testing zone 23.

With reference to FIG. 1B, a fluid sample is loaded by contacting the fluid sample with the inlet zone 21 on thread 20. The fluid sample is then transported through thread 20 by wicking action from the inlet zone 21 to intermediate zone 22. When the fluid sample reaches branching point 40, the fluid sample contacts testing threads 25, and a portion of the fluid sample is transported through testing threads 25 by wicking action to testing zones 26. A portion of the fluid sample is also wicked through intermediate zone 22 of thread 20 to testing zone 23.

In certain embodiments, testing zones 23 and 26 include the same detection reagent. In other embodiments, at least one of testing zone 23 and testing zones 26 includes a detection reagent that is different from the detection reagent on another testing zone. Preferably, testing zone 23 and testing zones 26 each include a unique detection reagent.

With reference to FIG. 1C, a fluid sample is loaded by contacting the fluid sample with the inlet zone 21 on thread 20. The fluid sample is transported through thread 20 from inlet zone 21 to intermediate zone 22 to testing zone 23 by wicking action. In certain embodiments, testing zones 23 include the same detection reagent. In other embodiments, at least one testing zone 23 includes a detection reagent that is different from the detection reagent on a second testing zone 23. In certain embodiments, inlet zones 21 are loaded simultaneously.

The "sewn array" configuration has several characteristics that are well-suited for assays. First, every pair of stitches (i.e., a portion of the thread that spans both sides of the substrate) can serve as a different assay. Second, the fluid sample travels a short distance and therefore the response of the device can be fast. Third, the "sewn array" can be incorporated into clothing, bandages, or diapers. The stitches close to the skin can serve as the inlet zones, while the stitches on the exterior side of the device can serve as the testing zones, where they can be easily observed in a non-intrusive manner.

Biological Samples

The diagnostic systems described herein can be used for assaying small volumes of biological samples, e.g., fluid samples. Biological samples that can be assayed using the diagnostic systems described herein include, e.g., urine, whole blood, blood plasma, blood serum, cerebrospinal fluid, ascites, tears, sweat, saliva, excrement, gingival cervicular fluid, or tissue extract.

In some embodiments, the volume of fluid sample to be assayed can be a drop of blood, e.g., from a finger prick, or a small sample of urine, e.g., from a newborn or a small animal.

Applications

The hydrophilic diagnostic threads described herein have many applications in modern medicine (e.g., in sports medicine, infant/child diagnostics, diabetes monitoring, military, underwater/diving monitoring, diagnostic dental floss, etc.). Additionally, the diagnostic systems described herein can be utilized in applications in which low cost is a concern, e.g., healthcare in the less-industrialized world, military and homeland security operations, environmental, on-site testing.

For example, hydrophilic diagnostic threads can be woven or knitted into clothing using existing technology, such as high-speed shuttleless weaving machines (e.g., at 2000 meters per minute). Such embodiments can provide, e.g., ubiquitous and continuous monitoring of subjects, such as soldiers in the field. In other embodiments, hydrophilic diagnostic threads can be woven into bandages.

In another embodiment, the diagnostic systems described herein can be used in diapers, e.g., to monitor premature babies. In one embodiment, a thread is located at the proper place inside the diaper, which leads to the external surface of the diaper. Urine is loaded into the inlet zone of the thread, which is then used to load diagnostic threads located on the external surface of the diaper, where colorimetric indicators can be read by a nurse/technician/doctor.

In other embodiments, diagnostic hydrophilic threads can be incorporated into paper or other assay mediums. For example, a thin sheet of paper can be placed between the protective laminates as the assay medium and the thread could be used to deliver the analyte to a precise location on the paper. For example, hydrophilic paper, patterned into channels with hydrophobic lines of polymer (as described in PCT/US07/081,848), can be used in combination with the threads described herein. In these devices, the flow of fluid is driven by capillarity.

The invention is further illustrated by the following examples. The examples are provided for illustrative purposes only. They are not to be construed as limiting the scope or content of the invention in any way.

EXAMPLES

Example 1

Preparation and Use of a "Woven Array" Diagnostic System

Thread

In some diagnostic systems, 100% cotton thread with a diameter of 0.3 mm was used (Cebelia Crochet Cotton Art G167, DMC, NJ, USA). This thread was of sufficient width to be enable analyte detection by the naked eye and reducing the loss of detection due to the presence of the analyte within the interior of the thread. The thread was manufactured by a process that included mercerization (exposure of a thread under tension to a NaOH bath, followed by neutralization with acid). This process increased the strength of the thread and its absorbency of water. The ability of Nylon thread (unwaxed dental floss, CVS Pharmacy Inc., RI, USA) and 100% polyester thread (McMaster-Carr, NJ, USA) to wick fluids was also tested. These artificial fibers may be well-suited for applications where transparency of the thread is needed to index-match with biological fluids.

Housings

In some of the diagnostic systems, the thread was encapsulated between two pieces of transparent, water-impermeable, polymer tape. The tape (i) acted as a substrate onto which the thread could be arranged and supported, (ii) served as a "handle" by which the device could be manipulated, labeled, stored, dispensed, and used, (iii) protected the assays from the environment; and, (iv) minimized evaporation, which could alter the concentration or rate of wicking of the analyte.

Two types of tape were tested: (i) multipurpose tape (Scotch®MultiTask Tape) and, (ii) vinyl tape with rubber adhesive backing (3M™ Vinyl Tape #471). The vinyl tape is able to make complete conformal contact with its substrate (in this case, the thread). The Scotch tape combines crystal clarity, strength and moisture resistance for performance over a wide range of taping tasks, but does not adhere conformally to the entire surface of the thread.

To ensure good contact between the tape and the thread, laminator (Pro-Etch laminator, Micro-Mark) was used. The laminator sandwiched the thread between two pieces of tape using heat and pressure. The laminator was used in its "hot mode" and used to laminate the tape and thread within seconds.

Device Preparation

Figure 5:
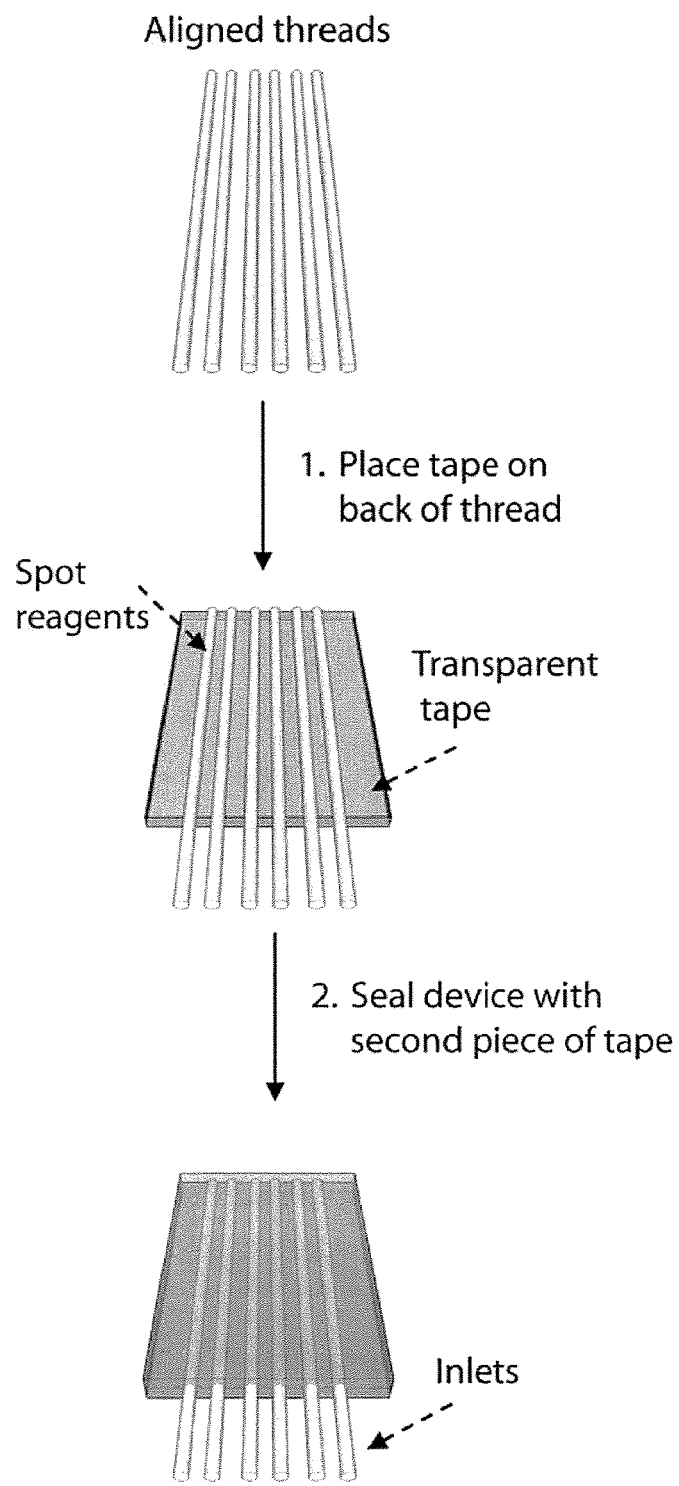
FIG. 5 is a schematic illustration of a method of making a "woven array" diagnostic system.
Figure 6:
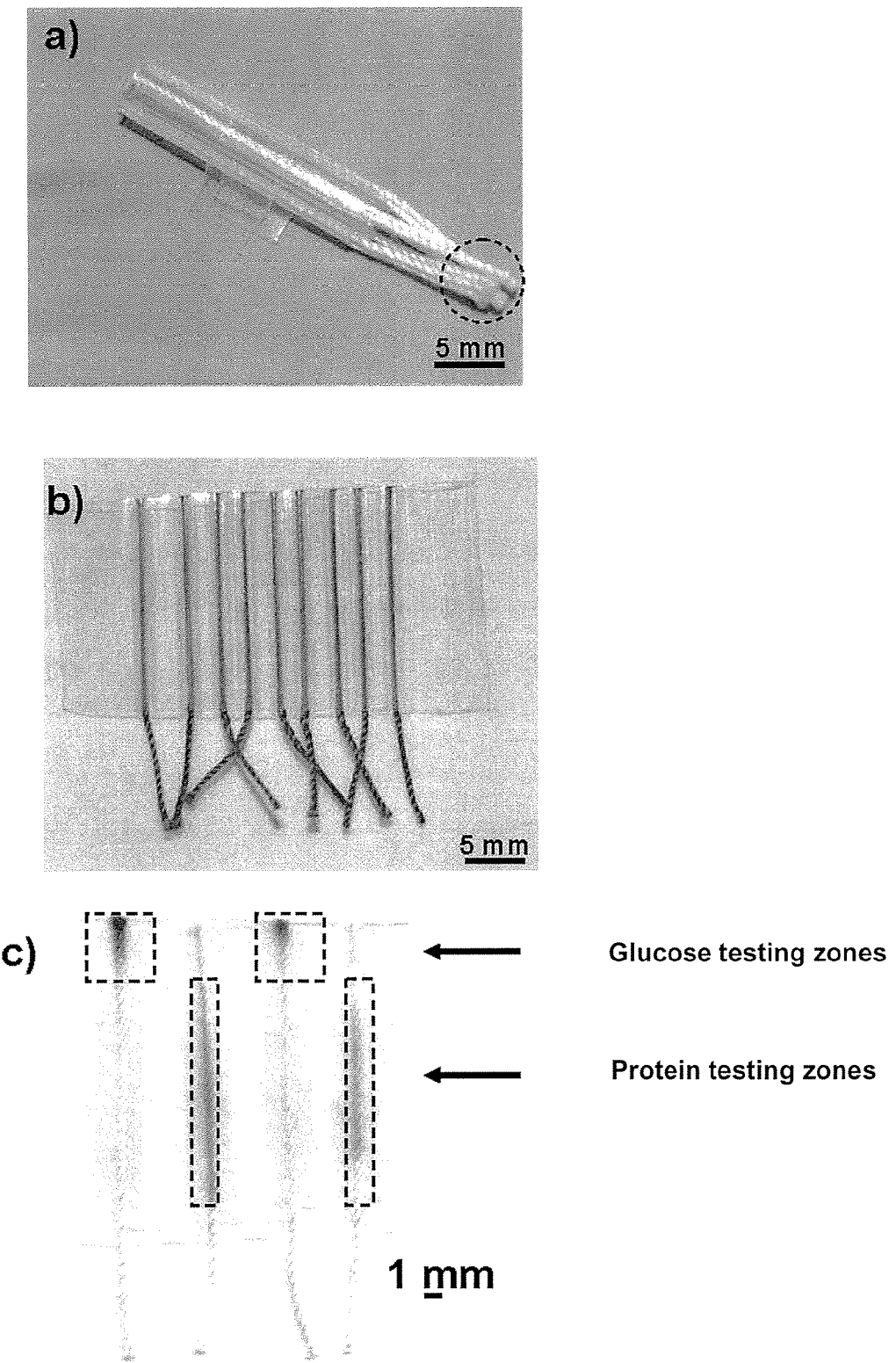
FIG. 6A is an image of a rolled "woven array" diagnostic system.
FIG. 6B is an image of an unrolled "woven array" diagnostic system after loading.
FIG. 6C is an image of a "woven array" diagnostic system used to assay for glucose and protein.

For the fabrication of the "woven array" device (depicted in FIG. 1A), a loom was used to arrange several threads in parallel to each other. The loom was made by installing steel pins (McMaster-Carr, NJ, USA) into a 1.5 cm thick Derlin block (two parallel rows of pins, 6 cm apart, with the pins in each row spaced by 0.5 cm). A piece of tape was inserted underneath the threads, the threads were pressed against the tape to make intimate contact between the tape and the thread, and a second piece of tape was pressed on top of the threads to encapsulate them between the two pieces of tape (FIG. 5). To disconnect the thread form the loom, the thread was cut where it contacted the pins of the loom and a laminator was used to make a better contact between the thread and the tape (FIG. 5). The threads of the device were cut such that one end of each piece of thread (i.e., "branch") protruded from the tape portion of the device and served as the inlet zone. To facilitate the application of the sample, the device was rolled such that the ends of the threads converged to a single point (FIG. 6A). The length of each thread that protruded from the device was long enough to allow their convergence.

Assays

The colorimetric assay for protein was based on the binding of tetrabromophenol blue (TBPB) to protein; TBPB changes from yellow to blue through the dissociation of phenolic hydroxyl groups at a pH of about 3 when a protein is present. For protein detection, a solution of 0.5 µL of 250 mM citric acid (pH 1.8) and 0.5 µL 3.3 mM tetrabromophenol blue (TBPB) in 95% ethanol was spotted onto the testing zone of the thread using a pipetman.

To detect glucose, the enzymatic oxidation of iodide to iodine was used; this reaction induces a color change from colorless to yellowish-brown in the presence of glucose. For this assay, 0.5 µl of 0.6 M solution of potassium iodide and 0.5 µL of a 1:5 horseradish peroxidase/glucose oxidase solution (15 units of protein per 1 ml of solution) was spotted onto the testing zone of the thread using a pipetman.

After spotting the reagents at the desired locations, the thread was laminated between two pieces of tape using a laminator (Pro-Etch laminator, Micro-Mark, USA).

To test the wicking properties of the woven array configuration, the tape portion of the device was rolled and the protruding ends of the threads (i.e., the inlet zones) were dipped in different volumes of red ink. To load a device composed of nine threads, about 30 µl of ink was used. The solution wicked along the threads rapidly, at a rate of about 2.5 cm/min (see FIG. 6B).

To test the ability to perform diagnostic colorimetric assays with the device, a pipette was used to spot the tip of each piece of thread (prior to encapsulating the thread with tape) with the reagents for colorimetric assays that detect the level of glucose and protein in urine. The reagents were dried in ambient conditions for about 1 hour. After spotting the reagents onto the thread, the device was sealed with another piece of tape, the device was disconnected from the loom, it was laminated it.

FIG. 6C, depicts a device 2 minutes after adding a 30 µl sample of artificial urine that contained 75 µM BSA and 500 mM glucose. Both assays were performed in duplicate and in parallel. When the sample was applied, the fluid wicked along the thread. The enzymatic reaction of the glucose assay required oxygen for its activity, and therefore color appeared at the end of the thread where it was exposed to air. TBPB reacted with the sample as soon as the sample reached the detection zone, and therefore a change in color was observed closer to the inlet zone.

The minimum detection levels were 2.5 mM for glucose and 0.5 µM for BSA (defined as the minimum concentration that generated a color response observable by the unaided eye). Color changes in the thread were apparent about 10 seconds after spotting the sample, and the colors reached their maximum intensity after 2 min. These response times are similar to those of conventional dipsticks.

Modifications to Threads

To improve the wicking properties (i.e., the speed in which the thread wicks fluids) of the thread, the thread was plasma oxidized for 5 minutes. This procedure improved the wicking properties of the thread from 1.25 cm/min to 2.5 cm/min. The wicking properties of Nylon threads and polyester threads were also examined. Both the Nylon thread and the polyester threads wicked at a rate of 5 cm/min. Although these threads wicked faster than cotton thread, their adherence to the tape was weaker than the cotton thread. Thus, these threads could be useful in devices that require faster wicking and do not entail the encapsulation of a thread within tape.

Figure 7:
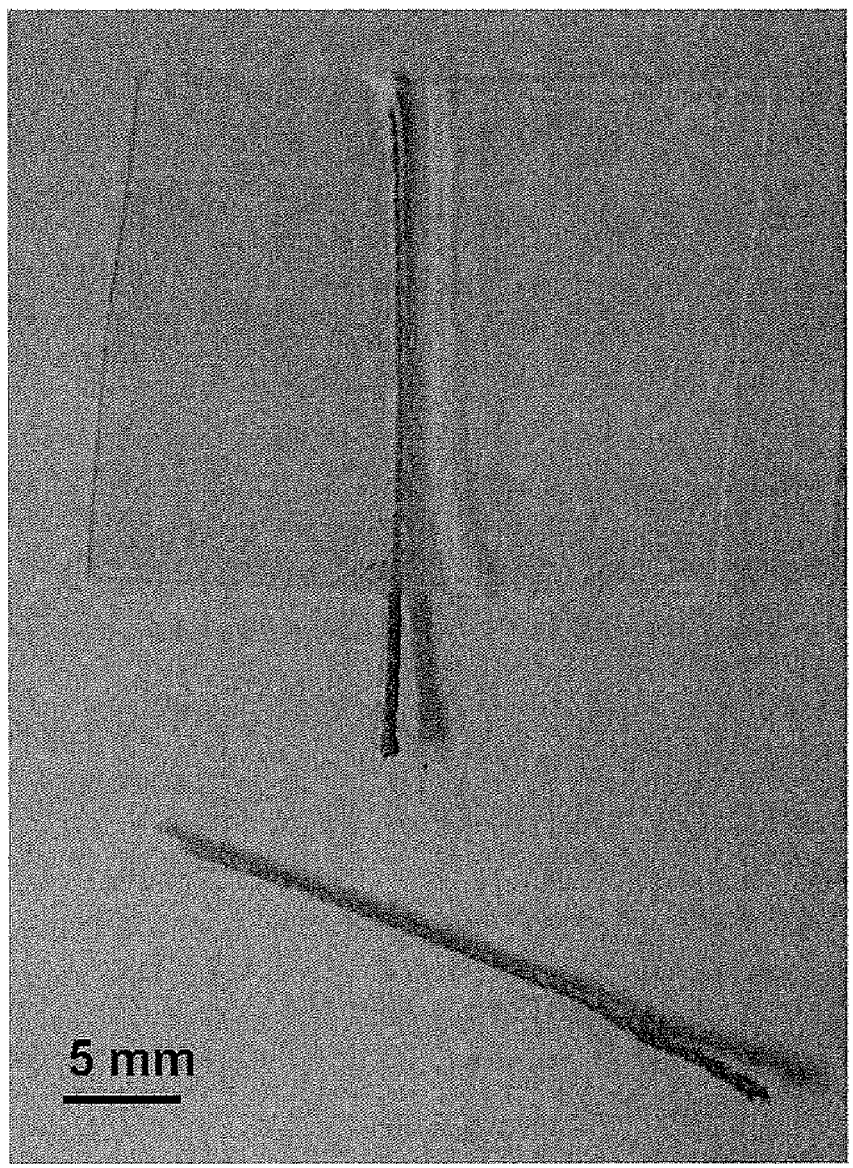
FIG. 7 is an image of a "woven array" diagnostic system of two threads coated with petroleum jelly.

In another method to modify the wicking properties of the thread, a hydrophobic coating (petroleum jelly or wax) was placed on the outer side of the hydrophilic thread. When the thread was subsequently laminated between two pieces of Scotch tape, wicking was observed only within the thread (FIG. 7). The use of petroleum jelly also facilitated removal of the thread from the encapsulating tape (FIG. 7). This method can be used to separate the thread from the tape for further analysis of the analytes on the thread.

Modifications to Housing

Different tapes were tested for their effects on the wicking properties of threads encapsulated within the tape. Both vinyl tape and clear Scotch tape were used to fabricate the woven device. When vinyl tape was used to fabricate the device, the tape softened upon lamination and formed a conformal seal around the threads. The Scotch tape, however, did not form a conformal seal and thus created a small gap between the tape adjacent to the thread.

Figure 4:
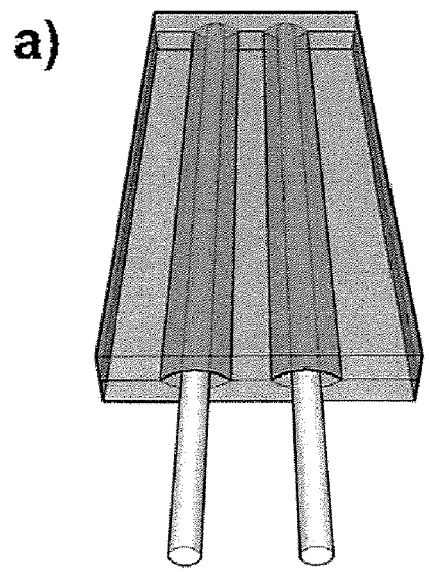
FIG. 4A is a schematic illustration of a "woven array" diagnostic system with a wider gap between the threads.
FIG. 4B is a schematic illustration of a "woven array" diagnostic system with a narrower gap between the threads.
Figure 4:
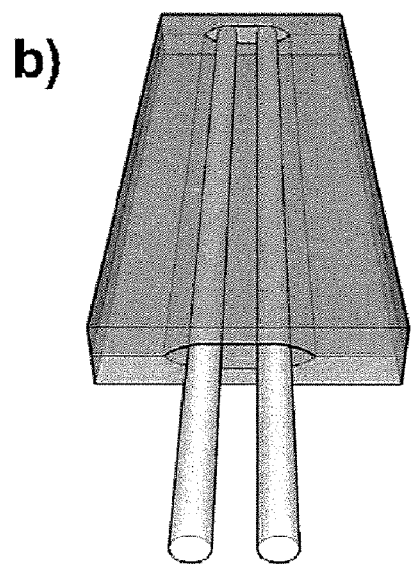
Figure 8:
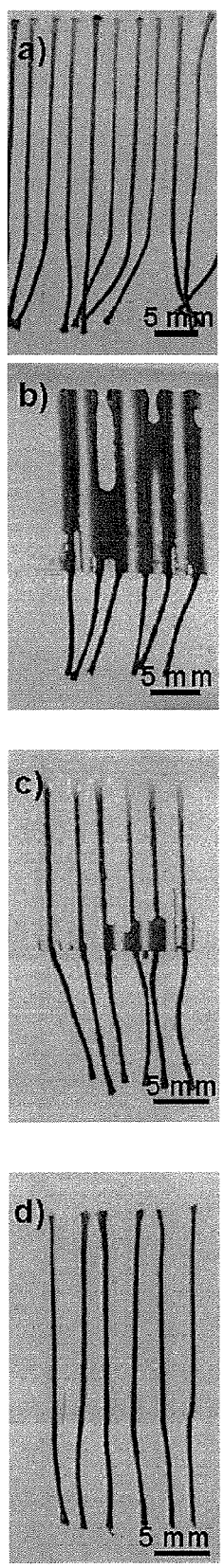
FIG. 8A is an image of a "woven array" diagnostic system of threads within a housing of two pieces of vinyl tape.
FIG. 8B is an image of a "woven array" diagnostic system of threads within a housing of two pieces of Scotch tape.
FIG. 8C is an image of a "woven array" diagnostic system of threads within a housing of one piece of Scotch tape and one piece of vinyl tape.
FIG. 8D is an image of a "woven array" diagnostic system of threads coated with petroleum jelly within a housing of two pieces of Scotch tape.

This difference between the tapes affected the wicking properties of the device. The difference was observed upon dipping the thread protruding from the tape, along with a small portion of the tape, into a solution of red ink (FIG. 8). The vinyl tape formed a tight seal with the thread. The seal ensured that the solution only wicked through the thread (which was observed under an optical microscope). The Scotch tape did not form a conformal seal around the threads, and the solution wicked both through the threads and though a small gap between the tape and the thread (see FIG. 8B and FIG. 4). This gap effectively formed a fluidic channel. The wicking through the gap was faster (6 cm/min) than the wicking through the thread (1.25 cm/min).

When the threads were laminated between one piece of Scotch tape and one piece of vinyl tape and the bottom of the device was submerged into the ink solution, the ink wicked through a gap between the tape and the thread. This gap was significantly smaller than the gap formed with the threads laminated between two pieces of Scotch tape (FIG. 8C).

No difference was seen between the wicking behavior of the two tapes when only the tips of the threads (and not the edge of the two pieces of tape) were dipped into a solution of red ink. For both devices, the threads wicked the ink solution.

Both types of contacts made by the tapes are useful. The conformal seal formed by the Vinyl tape ensures that wicking occurs only within the thread such that individual diagnostic assays remain separated and individually encapsulated. The small gap created by the Scotch tape is useful as a capillary to allow rapid wicking through an open-channel.

Example 2

Preparation and Use of a "Branching Array" Diagnostic System

A loom as described in Example 1 was used to weave thread into a "branching array" configuration (as illustrated in FIG. 1B). The "branching array" illustrated in FIG. 1B contains only one inlet zone, which may result in smaller error rate compared to the "woven array" design. However, the "woven array" configuration may have a faster response than that of the "branching array", because the distance from the inlet zone to the testing zone is shorter.

Figure 9:
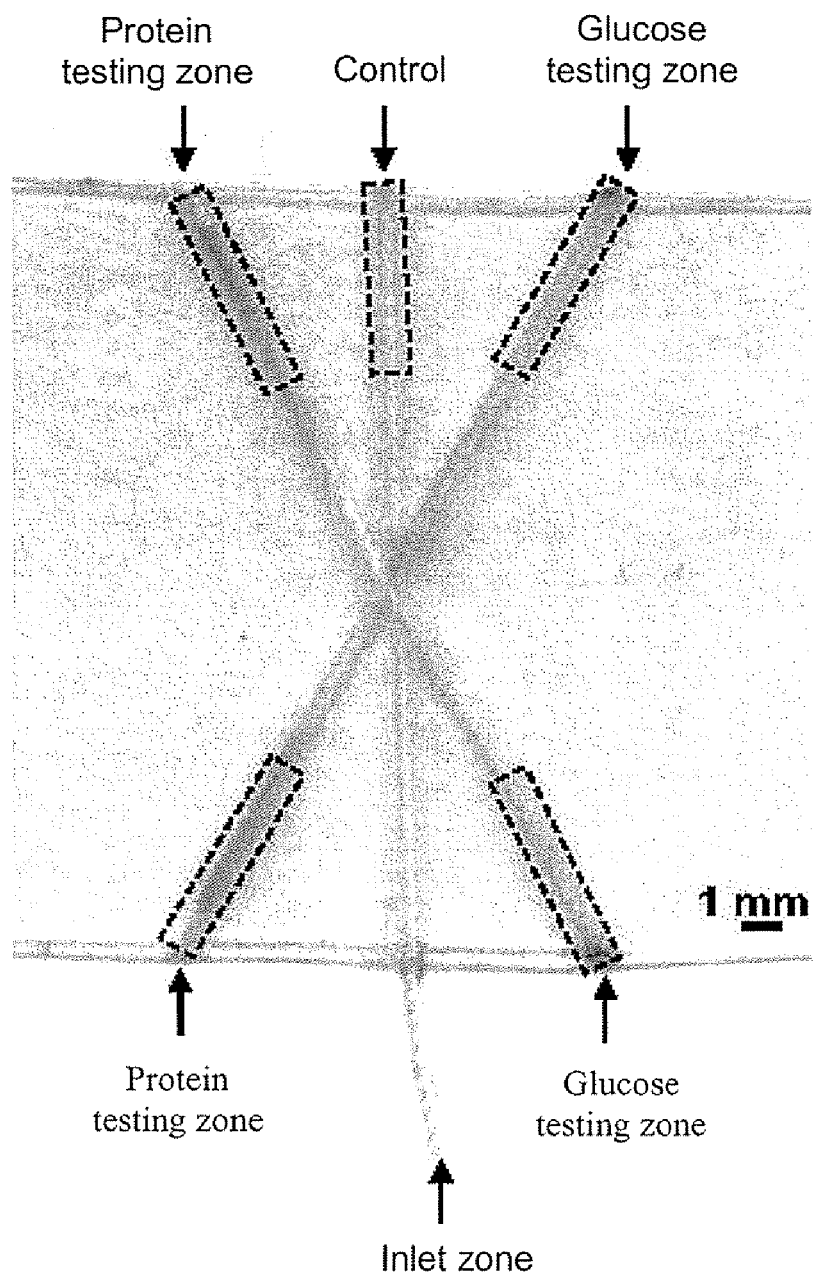
FIG. 9 is an image of a "branching array" diagnostic system loaded with a fluid sample and assayed for glucose and protein.

A branching array was used to run the colorimetric assays described in Example 1 (FIG. 9). Two factors were taken into consideration when determining the lengths of the threads for this device. First, the threads had to be long enough to prevent cross-contamination between the assays through the branching point. Second, the threads had to be longer than the distance that the diagnostic reagents traveled along the thread when preparing the testing zones.

When the detection reagents were spotted onto each thread, the detection reagents spread by capillary action a distance of about 0.5 cm towards the branching point. Based on this distance, the thread was made at least 2-3 times this length to ensure that no cross contamination would occur and that an intermediate zone existed between the inlet zone and the testing zone.

Example 3

Preparation of a "Sewn Array" Diagnostic System

A "sewn array" diagnostic system (as illustrated in FIG. 1C) was fabricated by sewing a thread with a needle into a 0.127 mm thick Mylar strip (about 2"×6"). The assays on two adjacent stitches were physically isolated by blocking every other hole (formed by the needle) in the Mylar with 3 µL droplets of clear nail polish. Another "sewn array" was fabricated by sewing threads into an all-purpose latex free plastic bandage (CVS Pharmacy, Inc., RI), using the small holes in the bandage as guidelines for sewing the threads.

One stitch on the bottom side of the substrate and one stitch on the upper side of the substrate constitute one assay (see FIG. 1C). The lower stitch (i.e., on the bottom face of the substrate) serves as the inlet zone and the upper stitch (i.e., on the top face of the substrate) serves as the testing zone (FIG. 1C). These two stitches were defined as one unit and isolated from the other stitches by applying a 3 µL drop of clear nail polish to block the holes (formed by sewing) in the substrate, and onto the thread located at these holes.

To test the wicking properties of the sewn array device, different volumes of red ink were introduced to the inlets. A volume of 0.5 µL was found to be sufficient to fill a segment of the thread.

Figure 10:
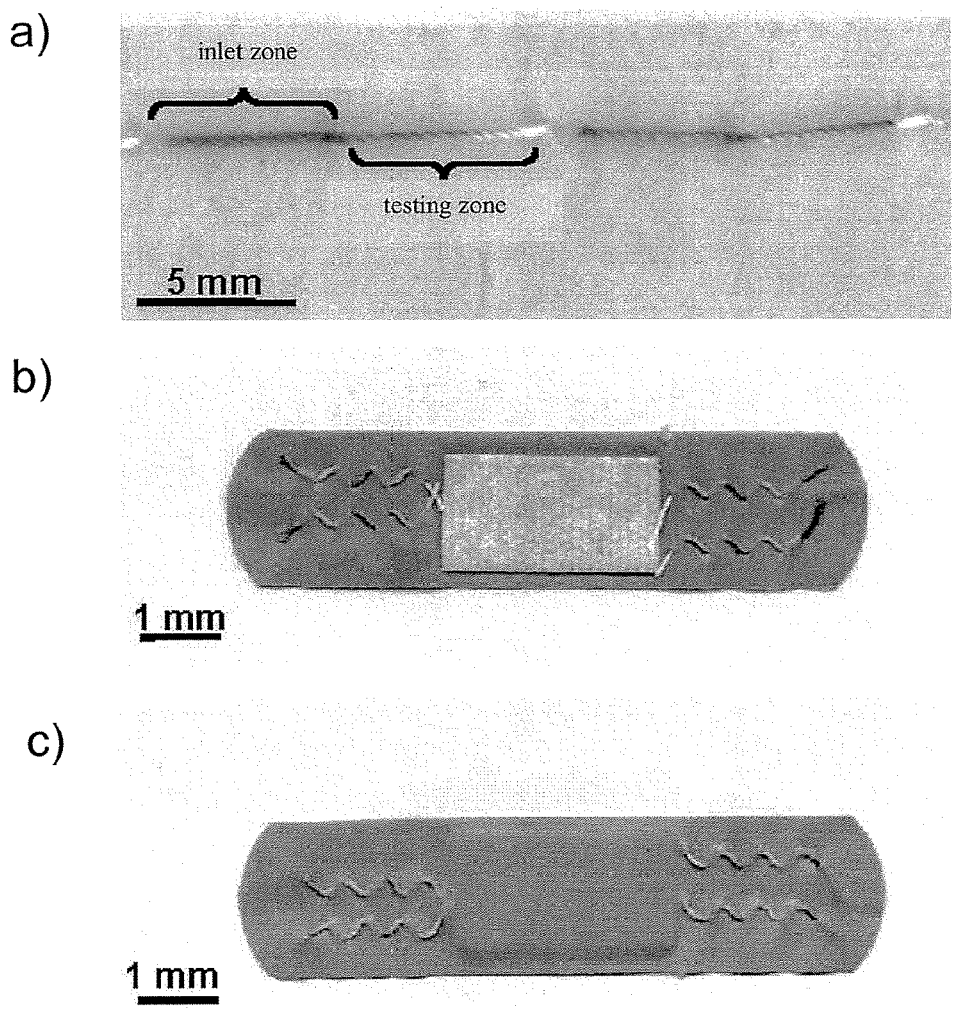
FIG. 10A is an image of a "sewn array" diagnostic system that includes a thread sewn through a Mylar sheet.
FIG. 10B is an image of the bottom side of a "sewn array" diagnostic system that includes two threads sewn through an adhesive bandage.
FIG. 10C is an image of the top side of a "sewn array" diagnostic system that includes two threads sewn through an adhesive bandage.

FIG. 10A depicts a Mylar strip with four stitches of thread. In FIG. 10A, the left two stitches formed one "assay unit", having an inlet zone on the bottom face of the strip and a testing zone on the top face of the strip. The second set of stitches on the right side of the strip formed a second "assay unit", with an inlet zone on the bottom face of the strip and a testing zone on the top face of the strip. The first and second assay units were separated by the application of clear nail polish at the hole formed by the thread passing through the strip at this point. Subsequently, 0.5 µL of a red dye was applied to the inlet zone of the first assay unit on the left, and 0.5 µL of a blue dye was applied to the inlet zone of the second assay unit on the left. As demonstrated in FIG. 10A, the individual assay units did not "bleed" together by capillary action.

The sewn array design is well-suited for assays embedded in bandages because one side of the device can absorb and wick fluid samples and transport them to a testing zone on the other side of the device. This concept was demonstrated by sewing thread into a bandage, isolating the "assay units" with clear nail polish, and applying dye to the inlet zones. FIG. 10B shows the bottom side of a device that made with a thread sewn into a latex free bandage while FIG. 10C shows the top side of the device.

Example 4

Using Diagnostic Systems to Assay Artificial Urine

Artificial urine was tested for the presence of four analytes: nitrite, glucose, ketone, and protein. A "woven array", a "branching array", and a "sewn array" were prepared as described herein. To detect nitrite, the thread was spotted with 0.5 uL-solution of 2 mg/mL sulfanilamide, 1.7 mg/ml 3-hydroxy-1,2,3,4-tetrahydrobenzo(h)quinoline and 25 mg/mL tartaric acid in methanol. To detect ketone, the thread was spotted with 0.5 uL solution of 20 mg/mL sodium phosphate, 20 mg/mL sodium borate, 10 mg/mL glycine, 0.5 uL solution of 20 mg/mL nitroprusside, 30 mg/mL polyethyleneglycol (PEG, Mw=2000), and 2 mg/ml polyacrylic acid (PAA, Mw=2000). To detect glucose and protein, the threads were spotted as described in Example 1. Artificial urine was prepared that contained 1 mM BSA, 200 mg/ml lithium acetate, 0.5 mM sodium nitrate, and 500 mM glucose.

Figure 11:
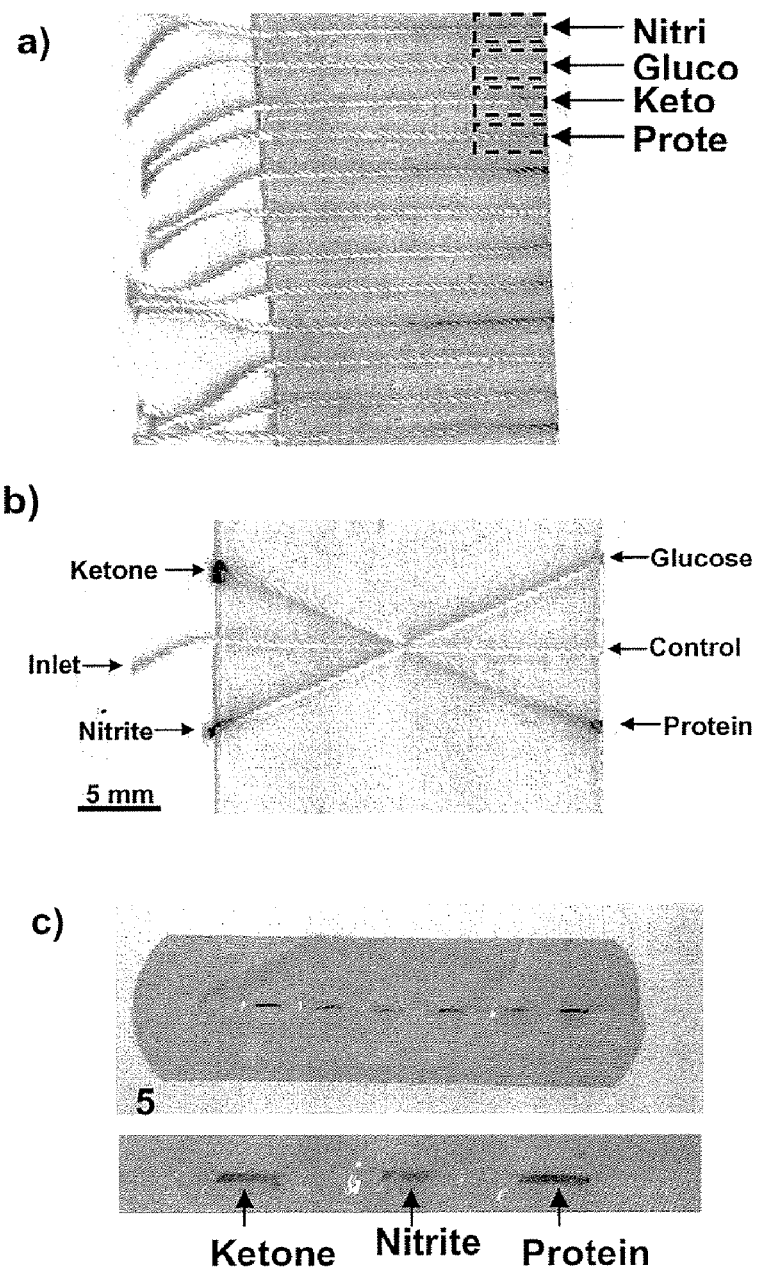
FIG. 11A is an image of a "woven array" diagnostic system used to detect various analytes.
FIG. 11B is an image of a "branching array" diagnostic system used to detect various analytes.
FIG. 11C is an image of a "sewn array" diagnostic system used to detect various analytes.

The diagnostic colorimetric assay was performed using the "woven array" device by rolling the device and contacting the joined inlet zones with 30 µL of artificial urine. As shown in FIG. 11A, all four analytes were detected.

The diagnostic colorimetric assay was performed using the "branching array" and "sewn array" devices by contacting the inlet zones with 15 µL and 0.5 µL of the artificial urine sample, respectively. As shown in FIGS. 11B and 11C, the analytes were detected using these two devices.

Equivalents

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A system for performing an assay on a sample comprising one or more hydrophilic testing threads defining a sample inlet zone at a proximal end, an intermediate zone distal to the inlet zone through which fluid sample is carried by capillary action, and a testing zone distal to the intermediate zone and comprising a detection reagent which reacts with a predetermined analyte to produce a detectable signal.

2. The system of claim 1 further comprising a housing for support of the hydrophilic testing thread.

3. The system of claim 1, wherein the signal is detectable by a naked eye or a spectrometer.

4. The system of claim 2 wherein at least a portion of the hydrophilic testing thread is enclosed within the housing to protect the hydrophilic testing thread from contamination and mechanical damage.

5. The system of claim 2 wherein the housing comprises two faces, and the hydrophilic testing thread is sewn into the housing and exposed on each face.

6. The system of claim 2 wherein the testing zone is enclosed within and visible from outside the housing.

7. The system of claim 1 wherein the detection reagent is a colorimetric detection reagent.

8. The system of claim 1 comprising an array of hydrophilic testing threads for performing multiple assays on a biological sample.

9. The system of claim 1 comprising a portion of a bandage or cloth.

10. The system of claim 1 comprising a portion of a woven array of hydrophilic testing threads.

11. The system of claim 2 comprising a portion of a woven array of hydrophilic testing threads.

12. The system of claim 1 wherein a said hydrophilic testing thread comprises multiple testing zones or multiple inlet zones.

13. The system of claim 2 wherein a said hydrophilic testing thread comprises multiple testing zones or multiple inlet zones.

14. The system of claim 1 for performing multiple assays on a sample further comprising
   a housing, a hydrophilic loading thread comprising an inlet zone outside the housing, where one or more said hydrophilic testing threads communicate with said loading thread and at least a portion of the testing threads is enclosed within the housing.

15. The system of claim 14 further comprising in a said testing zone a detection reagent which reacts with a predetermined analyte to produce a signal apparent to the naked eye.

16. The system of claim 14 wherein at least two testing zones comprise different detection reagents.

17. A method of detecting an analyte in a fluid sample, the method comprising contacting an inlet zone of a system of claim 1 with a sample to induce sample flow by capillary action to a said testing zone and visually observing a signal at said testing zone.

18. The method of claim 17 comprising visually observing a plurality of signals at multiple detection zones.

* * * * *